United States Patent [19]

Kamen

[11] Patent Number: 4,986,821
[45] Date of Patent: Jan. 22, 1991

[54] DROP DETECTION HOUSING WITH POSITIVE TACTILE SIGNALING

[76] Inventor: Dean L. Kamen, 46 Gage Rd., Bedford, N.H. 03102

[21] Appl. No.: 231,600

[22] Filed: Aug. 9, 1988

Related U.S. Application Data

[63] Continuation of Ser. No. 77,056, Jul. 17, 1987, abandoned, which is a continuation of Ser. No. 868,258, May 28, 1986, abandoned.

[51] Int. Cl.$^5$ .............................................. A61M 5/00
[52] U.S. Cl. ................................................... 604/251
[58] Field of Search ............... 604/251, 253, 254, 246, 604/65, 67

[56] References Cited

U.S. PATENT DOCUMENTS

| | | |
|---|---|---|
| D. 273,419 | 4/1984 | D'Alo et al. . |
| D. 279,602 | 7/1985 | D'Alo et al. . |
| D. 293,130 | 12/1987 | Ashie et al. ............................ D24/53 |
| 4,037,597 | 7/1977 | Forberg .................................. 604/251 |
| 4,038,982 | 8/1977 | Burke et al. . |
| 4,321,461 | 3/1982 | Walter, Jr. et al. .................... 604/65 |
| 4,346,606 | 8/1982 | Cannon et al. ......................... 73/861 |
| 4,397,648 | 8/1983 | Knute .................................... 604/253 |
| 4,533,350 | 8/1985 | Danby et al. .......................... 604/253 |
| 4,548,600 | 10/1985 | Ruschke ................................ 604/257 |
| 4,557,725 | 12/1985 | Heyne et al. ........................... 604/67 |
| 4,668,216 | 5/1987 | Martin et al. .......................... 604/30 |
| 4,694,856 | 9/1987 | Leibinsohn ............................ 604/257 |
| 4,718,896 | 1/1988 | Arndt et al. ........................... 604/253 |

FOREIGN PATENT DOCUMENTS

| | | |
|---|---|---|
| 0229354 | 7/1987 | European Pat. Off. . |
| 8335578 | 2/1987 | Fed. Rep. of Germany . |
| 2546068 | 11/1984 | France . |

OTHER PUBLICATIONS

Das Bedienteil und die Uhr des Grundig-Videorecords Video 2×4 super, F. Meierhofer, Grundig Technische Informationen 3-81, pp. 119–128.

*Primary Examiner*—Stephen C. Pellegrino
*Assistant Examiner*—Kathleen A. Daly
*Attorney, Agent, or Firm*—Bromberg & Sunstein

[57] ABSTRACT

A system is provided for the automatic, self-checking switching of a medical infusion controller among a plurality of modes of operation. A medical infusion controller has a plurality of pressure-sensitive switches, each of which corresponds to a different mode of operation. A drip chamber is provided with nub elements in one of a variety of possible configurations, each of which correspond to one of the pressure-sensitive switches on the controller. When the drip chamber is placed in the controller, the nub configuration activates the corresponding switch. If the controller detects an incorrect number of nubs, it delivers an error message.

14 Claims, 2 Drawing Sheets

DROP DETECTION HOUSING WITH POSITIVE TACTILE SIGNALING

This is a continuation of co-pending application Ser. No. 077,056 filed on Jul. 17, 1987 now abandoned which is a continuation of Ser. No. 868,258 filed May 28, 1986 now abandoned.

TECHNICAL FIELD

The present invention relates to intravenous infusion systems in general and in particular to switching means for setting medical infusion controllers.

BACKGROUND OF THE INVENTION

Medical infusion controllers now provide microprocessor control of intravenous fluid delivery rates. These devices include sensors that monitor fluid flow rate and then adjust that rate accordingly. Despite the automatic nature of these devices, they typically must be manually set by the operator to indicate to the microprocessor whether the particular infusion set in use contains a 10 cc or a 60 cc cannula. Thus, there is a potential for serious human error. One prior art device has a protruding spring-loaded retractable pin switch on the controller. 10-cc and 60-cc cannula drip chamber are distinguished by the presence or absence of an aperture to receive the pin. If the aperture is absent, the pin is urged into the retracted position. If the aperture is present, the pin fits into the aperture, and thus does not retract. The two pin positions are associated with two different modes of operation. It can be seen that there is room for error, inasmuch as misalignment or malfunction of the pin can cause incorrect data to be signalled to the controller, by either retracting even in the presence of an aperture, or by failing to retract even in the absence of an aperture.

DISCLOSURE OF INVENTION

The present invention provides a system for automatically switching the controller between the 10 cc cannula setting and the 60 cc cannula setting. Rather than the retractable pin switch in the prior art, the present invention provides a plurality of pressure activated switches on the controller. These switches are configured in such a way that the controller will be set to a desired mode of operation when one and only one switch is activated. When more or less than one switch is activated, the controller will deliver an error message to the user. Drip chambers with different sized cannulae are provided with nubs in one of a variety of configurations designed to set the controller's mode of operation to correspond with that particular drip chamber's cannula size. When the drip chamber is placed in the controller, the nub comes into contact with the appropriate switch and the controller is thereby set to the appropriate mode of operation.

Thus, the present system, which conveys a positive signal to the control based on the presence of a nub in a particular location, avoids the aforementioned potential for error in the prior art device. As discussed above, the controller will send an error message and/or enter into an alarm mode unless an affirmatively correct signal is received. Thus, unlike the prior art device, the present device will not operate if, for example, a drip chamber from another manufacturer is placed in the controller, or if some of the contact sites are misaligned.

DESCRIPTION OF SPECIFIC EMBODIMENTS

Figure 1:
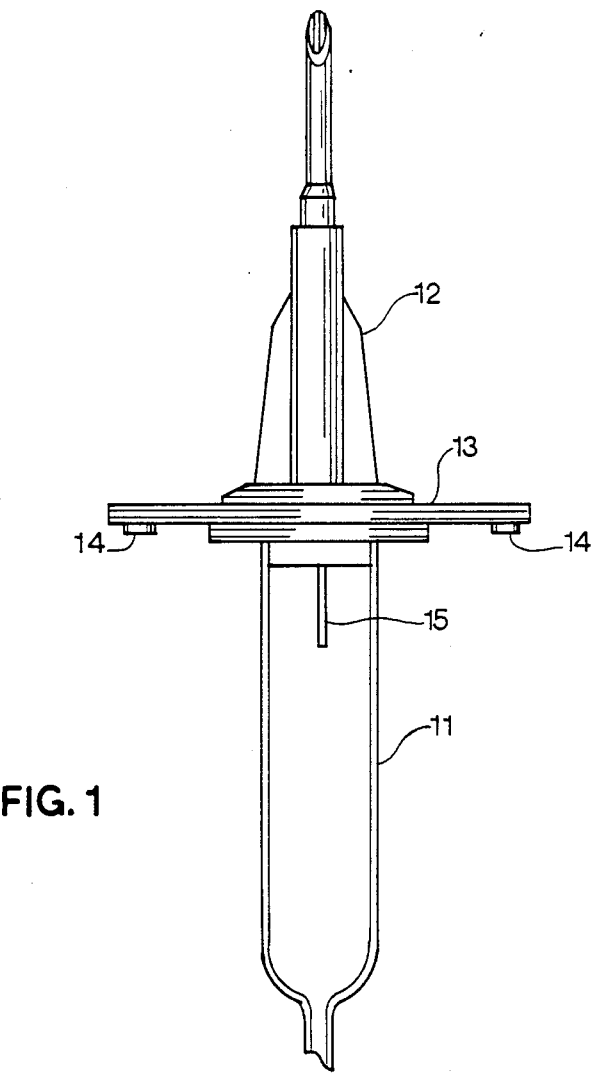
FIG. 1 shows a side elevational view of one possible embodiment of a drip chamber assembly according to the present invention.

FIG. 1 shows one possible embodiment of the present invention. The drip chamber 11 with cannula 15 and spike element 12 is provided with a flange element 13. The flange element is provided with a pair of nubs 14 that are disposed in such a way that whichever side of the flange is presented to a medical infusion controller, the nub on that side of the flange is located in the same relative position.

Figure 2:
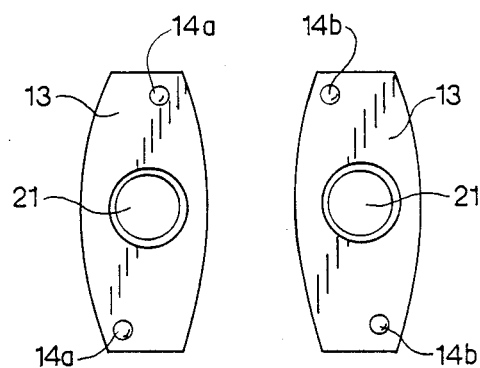
FIG. 2 shows a elevational view from above of the flange element of the drip chamber assembly shown in FIG. 1.

This will be better understood in FIG. 2, which shows two possible configurations of nubs on the flange element. It will be seen that the nubs are radially symmetric to each other around the center of the drip chamber area 21. Thus, regardless of which end of the flange is up, nub 14a will always be in the righthand corner and nub 14b will always be in the lefthand corner.

Figure 3:
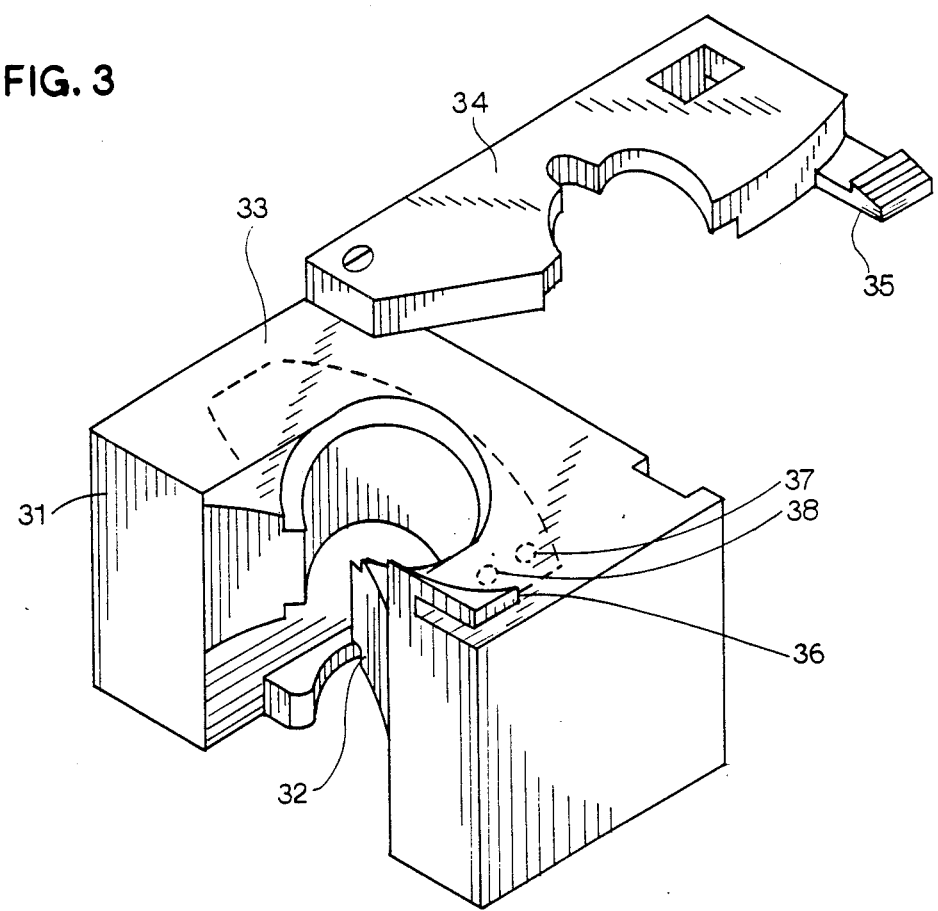
FIG. 3 shows a perspective view from above of one possible medical infusion controller for use with the drip chamber assembly shown in FIG. 1.

FIG. 3 shows a possible medical infusion controller for use in conjunction with the drip chamber shown in FIG. 1. The body 31 of the controller is provided with an aperture 32 for receiving the drip chamber. Surface 33 of the controller receives the flange element. The flange element is held in place by hinged retaining element 33, the end of which 35 locks into mating element 36. The mode of operation of the controller is set by the actuation of either switch 37 or 38. Although two switches are shown, the invention would apply to any number of switches greater than one.

Using means well known in the art, the controller is designed to enter one of various modes of operation upon the activation of exactly one switch. When more or less than one switch is activated, the controller will deliver an error message to the user. It would be possible as well for the controller to enter an alarm mode.

In the present embodiment, it is contemplated to use the switching system to switch the controller to either a mode of operation appropriate to a 10-cc cannula or to a mode of operation appropriate to a 60-cc cannula. However, it will be clear that the inventive concept is not limited to switching to these two particular modes of operation. The switching system could be modified to include a greater number of nubs in a variety of configurations, thus enabling foolproof switching to one of a potentially large number of mode settings. Further, the modes of operation governed by the switching system are not limited to cannula size. Conceivably, they could include content of the infusion bag, maximum flow rate, model of controller that is expected, characteristics of flow desired for a given class of patient, etc.

Because of the automatic setting of the controller, and the error message delivered upon presentation of an inappropriate nub number or configuration, the present system provides a safety device. It will be readily apparent that the system guards against undesired settings resulting either from human error or from those errors resulting from the use of retractable pin-type switches discussed earlier.

Figure 4:
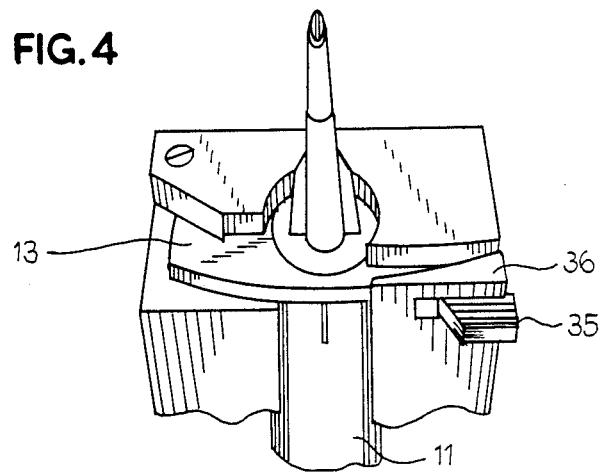
FIG. 4 shows a perspective view from above of the drip chamber of FIG. 1 placed in the medical infusion controller of FIG. 3.

FIG. 4 shows the drip chamber of FIG. 1 placed in the controller of FIG. 3. The nub on the side of the flange element over the switches is urged onto the corresponding switch by retaining element 34. As can be seen, it makes no difference which side of the flange element is over the switches. As discussed above, because of the symmetry of the flange element and the symmetrical configuration of the nubs on the flange element, either side of the flange element causes the activation of the same switch, and thus produces the same setting of the controller's mode of operation.

What is claimed is;

1. A medical infusion controller switching kit comprising:
    a first drip chamber having a body and having a first flange extending from said body, said first flange having a first pair of nubs disposed in a first pair of locations, said first drip chamber being designed to form drops of a first size;
    a second drip chamber having a body and having a second flange extending from said body, said second flange having a second pair of nubs disposed in a second pair of locations different from said first pair of locations, said second drip chamber being designed to form drops of a second size;
    a switch set having a first pressure-sensitive element disposed in a first switching location corresponding to one of said first pair of predetermined locations of said nubs on said first flange, said switch set also having a second pressure-sensitive element disposed in a second switching location corresponding to one of said second pair of predetermined locations of said nubs on said second flange;
    means for mounting one of said drip chambers in said switch set in a single orientation only to urge one of said nubs against a corresponding pressure sensitive element to activate said element; and
    signal processing means, responsive to the switch set for causing the system to enter into one of a plurality of predetermined standard modes of operation depending on which pressure-sensitive element in the switch set is activated.

2. A medical infusion controller kit as recited in claim 1 wherein each of said drip chambers are cylindrical, said first flange and said second flange each extend radially outwardly from opposite sides of said respective bodies, and each nub of one of said pairs of nubs disposed on said flange on opposite sides of said respective body in such a way that whichever side of said body is presented to said means for mounting, said nub on said flange on that side of said body is located in the same relative position with respect to said pressure sensitive elements.

3. A medical infusion controller switching kit, comprising:
    a first drip chamber having a body and having a first flange extending from said body, said first flange having a first nub in a first location;
    a second drip chamber having a body and a second flange extending from said body, said second flange having a second nub in a second location, said first and said second locations being different from one another with respect to their respective flanges;
    a switch set having a first pressure-sensitive element disposed in a first switching location corresponding to the first nub location, said switch set also having a second pressure-sensitive element disposed in a second switching location corresponding to the second nub location;
    means for mounting one of said drip chambers in said switch set to urge said respective nub against a corresponding pressure-sensitive element to activate said element; and
    signal processing means, responsive to the switch set for causing the system to enter into one of a plurality of predetermined standard modes of operation depending on which pressure-sensitive element in the switch set is activated.

4. A medical infusion controller kit as recited in claim 3 wherein each of said drip chambers are cylindrical, each of said flanges extend radially outwardly from opposite sides of their respective bodies, said first flange comprises a first nub configuration including said first nub, said second flange comprises a second nub configuration including said second nub, wherein a plurality of sides of each of said drip chambers may alternately be mounted in said switch set.

5. A medical infusor controller kit as recited in claim 3, wherein the controller enters into an alarm mode if other than exactly one pressure-sensitive element is activated.

6. A medical infusor controller kit according to claim 5 wherein each of said drip chamber flanges include a plurality of wing members, each of which present an identically configured nub set to said switch set.

7. A medical infusor controller kit according to claim 6 including exactly two wing members symmetrically disposed about said chamber.

8. A medical infusion controller kit as claimed in claim 3, wherein said first drip chamber has a first size of cannula and said second drip chamber has a second size of cannula, said first size of cannula being different from said second size of cannula.

9. A medical infusion controller switching kit, comprising:
    a first drip chamber having a body and having a first flange extending from said body, said first flange having a first nub in a first location, said first chamber being designed to form drops of a first size;
    a second drip chamber having a body and a second flange extending from said body, said second flange having a second nub in a second location, said second drip chamber being designed to form drops of a second size, said first and said second locations being different from one another with respect to their respective flanges;
    a switch set having a first pressure-sensitive element disposed in a first switching location corresponding to the first nub location, said switch set also having a second pressure-sensitive element disposed in a second switching location corresponding to the second nub location;
    means for mounting one of said drip chambers in said switch set to urge said respective nub against a corresponding pressure-sensitive element to activate said element; and
    signal processing means, responsive to the switch set for causing the system to enter into one of plurality of predetermined standard modes of operation depending on which pressure-sensitive element in the switch set is activated.

10. A medical infusion controller for receiving a drip chamber and monitoring the flow of fluid therethrough, the drip chamber having a body, a flange having a predetermined number of nubs disposed in one of a predetermined set of patterns, said flange extending from the body and a cannula, the cannula being one of several sizes, the controller, comprising:
- a switch set having a set of pressure-sensitive elements corresponding in position to all predetermined locations on the flange of the drip chamber where a nub may be located;
- mounting means for affixing the drip chamber in the controller, such that the nubs on the drip chamber flange are urged against the switch set such that nubs in the predetermined locations actuate corresponding pressure-sensitive elements; and
- signal processing means, responsive to the switch set, for causing the controller to enter into one of a plurality of predetermined standard modes of operation depending upon which pressure-sensitive elements in the switch set actuated,
- such that, (i) if a first predetermined pattern of pressure-sensitive elements is actuated, the controller will enter into a mode of operation corresponding to a drip chamber having a first cannula size being affixed in the mounting means, (ii) if a second predetermined pattern of pressure-sensitive elements is actuated, the controller will enter into a mode of operation corresponding to a drip chamber having a second cannula size being affixed in the mounting means, (iii) and, if none of the pressure-sensitive elements are actuated or if the pressure-sensitive elements are not actuated in a predetermined pattern, the controller will enter into an alarm mode.

11. A medical infusion controller according to claim 10, wherein each predetermined pattern of actuated pressure-sensitive elements consists of exactly one pressure-sensitive element, and wherein the signal processing means includes means for recognizing as a predetermined pattern the actuation of one and only one pressure-sensitive element.

12. A medical infusion controller according to claim 10, wherein the number of predetermined standard modes of operation is two, one of such modes based respectively on a drip chamber with a 10-cc cannula and the other of such modes based on a drip chamber with a 60-cc cannula, and, consistent therewith, there are two predetermined patterns of actuated pressure-sensitive elements.

13. A method of communicating to a controller the size of a cannula in a drip chamber, the method comprising:
   (a) providing a drip chamber having:
      a body,
      a cannula mounted within the body, and a flange mounted transversely to the body; and
   (b) placing a nub on the flange in one of at least two predetermined locations for encoding the size of the cannula, the location of the nub encoding the size of the cannula.

14. A method according to claim 13, wherein: step (a) includes the step of providing a drip chamber having a flange with first and second symmetrically disposed members mounted transversely to the body; and
   step (b) includes the step of placing a nub in one of at least two predetermined locations on each member, the nub and the locations on the first member being symmetrically disposed in relation to the nub and the locations on the second member.

* * * * *